(12) United States Patent
Butterworth et al.

(10) Patent No.: US 7,827,989 B2
(45) Date of Patent: Nov. 9, 2010

(54) MECHANICAL DOSES COUNTER FOR A POWDER INHALER

(75) Inventors: Noel Butterworth, Holmes Chapel (GB); Stephen John Minshull, Holmes Chapel (GB); Simon Paul Wells, London (GB); Duncan Grant Young, London (GB)

(73) Assignee: Aventis Pharma Limited, West Malling (GB)

( * ) Notice: Subject to any disclaimer, the term of this patent is extended or adjusted under 35 U.S.C. 154(b) by 415 days.

(21) Appl. No.: 12/050,495

(22) Filed: Mar. 18, 2008

(65) Prior Publication Data

US 2008/0210226 A1 Sep. 4, 2008

Related U.S. Application Data

(63) Continuation of application No. PCT/GB2006/050287, filed on Sep. 12, 2006.

(30) Foreign Application Priority Data

Sep. 20, 2005 (GB) .................................. 0519151.1

(51) Int. Cl.
*A61M 11/00* (2006.01)
(52) U.S. Cl. ............................ 128/205.23; 128/203.15; 116/299; 235/66; 235/116; 235/118
(58) Field of Classification Search ............ 128/200.24, 128/203.15, 203.23, 205.23; 116/299, 314, 116/317; 222/23, 29; 235/66, 116, 118
See application file for complete search history.

(56) References Cited

U.S. PATENT DOCUMENTS

| 4,011,829 A | 3/1977 | Wachsmann et al. |
|---|---|---|
| 4,528,933 A | 7/1985 | Allen et al. |
| 4,565,302 A | 1/1986 | Pfeiffer et al. |
| 5,009,338 A | 4/1991 | Barker et al. |
| 5,176,132 A | 1/1993 | Drought et al. |
| 5,678,538 A | 10/1997 | Drought et al. |
| 5,687,710 A | 11/1997 | Ambrosio et al. |
| 5,740,792 A | 4/1998 | Ashley et al. |
| 5,829,434 A | 11/1998 | Ambrosio et al. |
| 5,988,496 A | 11/1999 | Bruna et al. |

(Continued)

FOREIGN PATENT DOCUMENTS

WO WO 94/14492 7/1994

(Continued)

*Primary Examiner*—Steven O Douglas
(74) *Attorney, Agent, or Firm*—Serena Farquharson-Torres

(57) ABSTRACT

A rotatably actuated counter is disclosed. The counter includes a ratchet driven unit wheel nested within a tens wheel. Each wheel has a radial face displaying counting indicia. The tens wheel is transparent, allowing the indicia on the unit wheel to be viewed adjacent to the indicia on the tens wheel to provide a total count. A slave wheel is positioned between the unit and tens wheels. A gear on one face of the slave wheel engages gear teeth on the tens wheel. A Geneva mechanism on the other face is engaged by a foot on the unit wheel once per rotation. The wheels are rotatably mounted within a housing having a sidewall with a window through which the count indicia may be viewed. The unit wheel rotates in ten increments and then rotates the tens wheel through one increment by engaging and rotating the slave wheel.

20 Claims, 9 Drawing Sheets

U.S. PATENT DOCUMENTS

| | | | |
|---|---|---|---|
| 6,076,521 | A | 6/2000 | Lindahl et al. |
| 6,182,655 | B1 | 2/2001 | Keller et al. |
| 6,240,918 | B1 | 6/2001 | Ambrosio et al. |
| 6,273,085 | B1 | 8/2001 | Eisele et al. |
| 6,484,717 | B1 | 11/2002 | Dagsland et al. |
| 6,701,917 | B2 | 3/2004 | O'Leary et al. |
| 6,752,153 | B1 | 6/2004 | Eckert et al. |
| 6,761,161 | B2 | 7/2004 | Scarrott et al. |
| 7,322,352 | B2 * | 1/2008 | Minshull et al. ....... 128/203.15 |
| 7,726,555 | B2 * | 6/2010 | Minshull et al. .............. 235/66 |

FOREIGN PATENT DOCUMENTS

| | | |
|---|---|---|
| WO | WO 95/34874 | 12/1995 |
| WO | WO 96/16687 | 6/1996 |
| WO | WO 97/20589 | 6/1997 |
| WO | WO 97/30743 | 8/1997 |
| WO | WO 98/41257 | 9/1998 |
| WO | WO 98/41258 | 9/1998 |
| WO | WO 99/49920 | 10/1999 |
| WO | WO 01/31578 | 5/2001 |
| WO | WO 02/053295 | 7/2002 |
| WO | WO 2004/026380 A2 | 4/2004 |
| WO | WO 2005/002654 | 1/2005 |

* cited by examiner

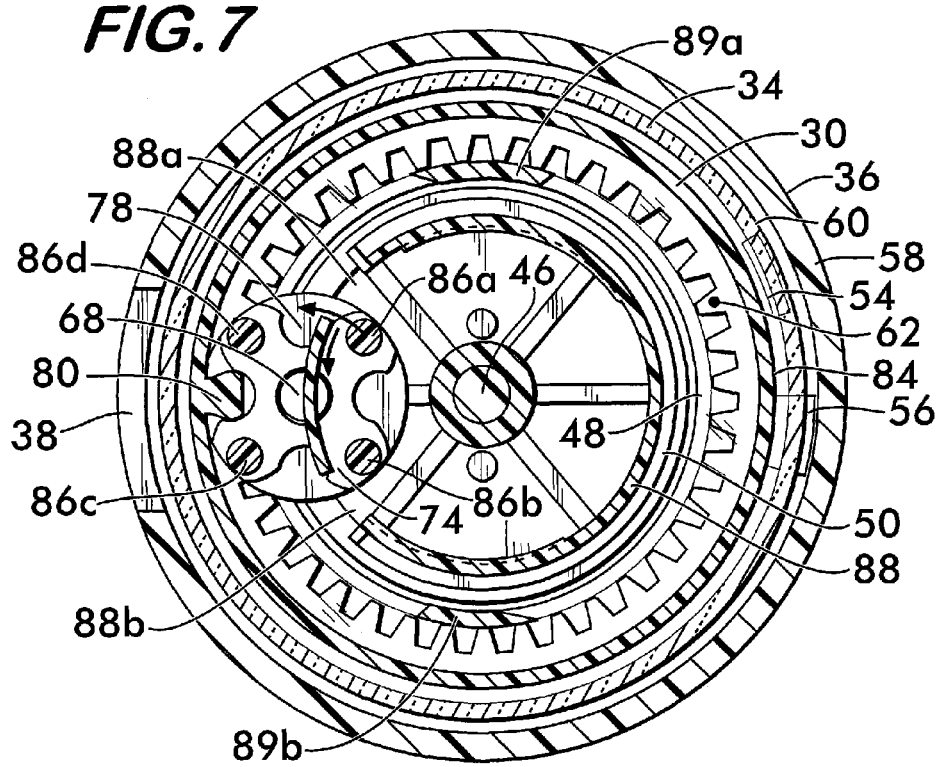
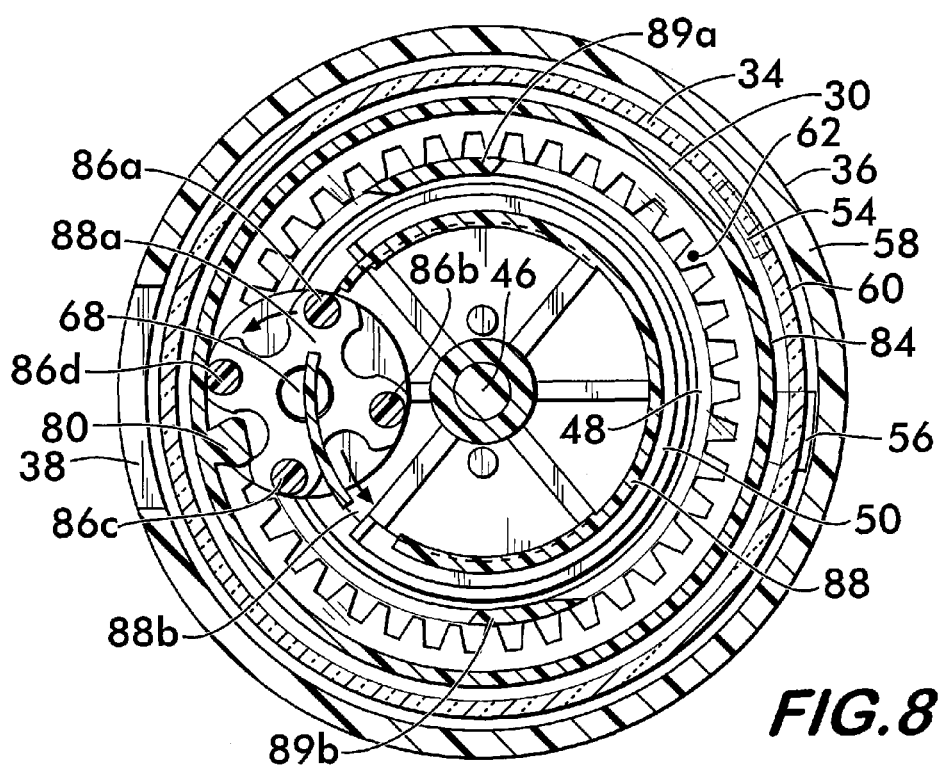

US 7,827,989 B2

MECHANICAL DOSES COUNTER FOR A POWDER INHALER

FIELD OF THE INVENTION

This invention concerns delivery devices for the delivery of metered doses of medicament, and counters associated with the devices for counting and displaying the number of doses administered or remaining within the inhaler.

BACKGROUND OF THE INVENTION

Oral delivery of medicaments to treat disorders such as asthma, emphysema and chronic bronchitis has been, for many years, reliably and effectively accomplished through the use of pressurized metered dose inhalers (PMDIs). Such inhalers provide a stream of atomized medicament inhaled directly into the affected air passageways and lungs to afford rapid relief from the symptoms of such disorders.

As an alternative to PMDIs, dry powder inhalers (DPIs) have received considerable attention because of their propellant-free composition and their relative ease of operation compared to PMDIs. DPIs can be used for oral and nasal administration and may be presented with the drug formulation pre-metered as capsules (unit-dose inhaler), blisters and cartridges (multi-unit dose inhaler) or as bulk material in a reservoir (multi-dose inhalers).

A necessary design feature of PMDIs and multi-dose DPIs is that they contain more formulation than strictly required to expel the labeled number of actuations/doses. A potential problem which may be particularly acute for PMDIs is dose inconsistency beyond labeled number of actuations/doses. A patient unknowingly using a PMDI or multi-dose DPI beyond the recommended number of doses may risk not receiving the correct drug dose with possibly dangerous consequences.

To avoid this problem, it is desirable to include a counter or indicator integrally with the inhaler to count and display to the user the number of doses remaining within the inhaler. This will allow the user sufficient warning as to when the inhaler is running low and should, therefore, be replaced so as to avoid the potential for sub-therapeutic dose administration. The counter or indicator should be simple in design, reliable in operation and easy to read and interpret.

SUMMARY OF THE INVENTION

The invention concerns a rotatably actuated counter mechanism useable, for example, with a dry powder inhaler for keeping track of doses administered or remaining. The mechanism comprises a first wheel rotatable about a first axis of rotation. The first wheel has a first display surface that extends circumferentially around the wheel for displaying counting indicia thereon. The first wheel also has a plurality of gear teeth extending circumferentially therein. A second wheel is also rotatable about the first axis. The second wheel has a second surface that extends circumferentially around it for displaying counting indicia thereon. The second wheel has a wall projecting in a direction substantially parallel to the first axis. The wall substantially surrounds the first axis and has a plurality of openings therethrough. The second wheel also has a foot projecting therefrom in a direction substantially parallel to the first axis. A slave wheel is positioned between the first and second wheels. The slave wheel is rotatable about a second axis of rotation that is offset laterally from the first axis. A gear is positioned on one face of the slave wheel. The gear is engaged with the gear teeth of the first wheel. The first wheel is rotated about the first axis upon rotation of the slave wheel about the second axis. A Geneva mechanism is positioned on an opposite face of the slave wheel. The Geneva mechanism has a plurality of receptacles adapted to receive the foot projecting from the second wheel. Engagement of the foot with one of the receptacles incrementally rotates the slave wheel in response to rotation of the second wheel and thereby incrementally rotates the first wheel. A plurality of pins are mounted in spaced relation around the Geneva mechanism. The pins project in a direction parallel to the second axis and are engageable with the wall. The pins align with and pass through the openings in the wall when the foot engages one of the receptacles. The pins otherwise engage the wall. Engagement of the pins and the wall prevent rotation of the slave wheel and thereby the first wheel as well, unless the foot is engaged with one of the receptacles and the opening in the wall is aligned with the pins.

Preferably the first wheel is positioned in overlying relation with the second wheel. The first display surface is transparent and surrounds the second display surface. Each of the indicia on the first display surface represent ten units, and each of the indicia on the second surface represent one unit. The indicia on the surfaces cooperate to indicate a total number of units counted by the counter.

The counter mechanism is preferably contained within a housing having a bottom. The first wheel is rotationally supported on the bottom. An axle extends from the bottom and is oriented coaxially with the first axis of rotation. The second wheel is rotatably mounted on the axle. An offset axle extends from the bottom and oriented coaxially with the second axis of rotation. The slave wheel is rotatably mounted on the offset axle. A sidewall is attached to the bottom and surrounds the first and second wheels. A window is positioned within the sidewall. Indicia on the first and second wheels are visible through the window, the visible indicia being indicative of a count registered by the counter.

Preferably the second wheel rotates through ten increments (360°) for every one incremental rotation of the first wheel.

The invention also includes a mechanism. The mechanism comprises a slave wheel rotatable about an axis of rotation. The slave wheel has first and second faces oppositely disposed. The axis of rotation is oriented substantially perpendicular to the faces of the slave wheel. A toothed gear is mounted on the first face of the slave wheel. The teeth project substantially radially outwardly from the axis. A Geneva mechanism is mounted on the second face of the slave wheel. The Geneva mechanism has a plurality of receptacles that extend in spaced relation circumferentially around it. Each receptacle has an opening facing substantially radially outwardly from the axis of rotation. A plurality of pins are positioned on the Geneva mechanism between the receptacles. The pins project in a direction substantially parallel to the axis of rotation.

The invention also includes a dry powder inhaler for administering a dose of a medicament. The inhaler comprises a reservoir holding the medicament and an air channel assembly engaged with and rotatably movable relatively to the reservoir for receiving the dose of medicament upon the relative motion. The inhaler also includes a rotatably actuated counter mechanism for counting a number of doses dispensed or remaining in the reservoir as described above.

BRIEF DESCRIPTION OF THE DRAWINGS

FIGS. 6-10 are cross-sectional views taken at line 6-6 in FIG. 4A illustrating the operation of the counter.

DETAILED DESCRIPTION OF THE PREFERRED EMBODIMENTS

Figure 1:
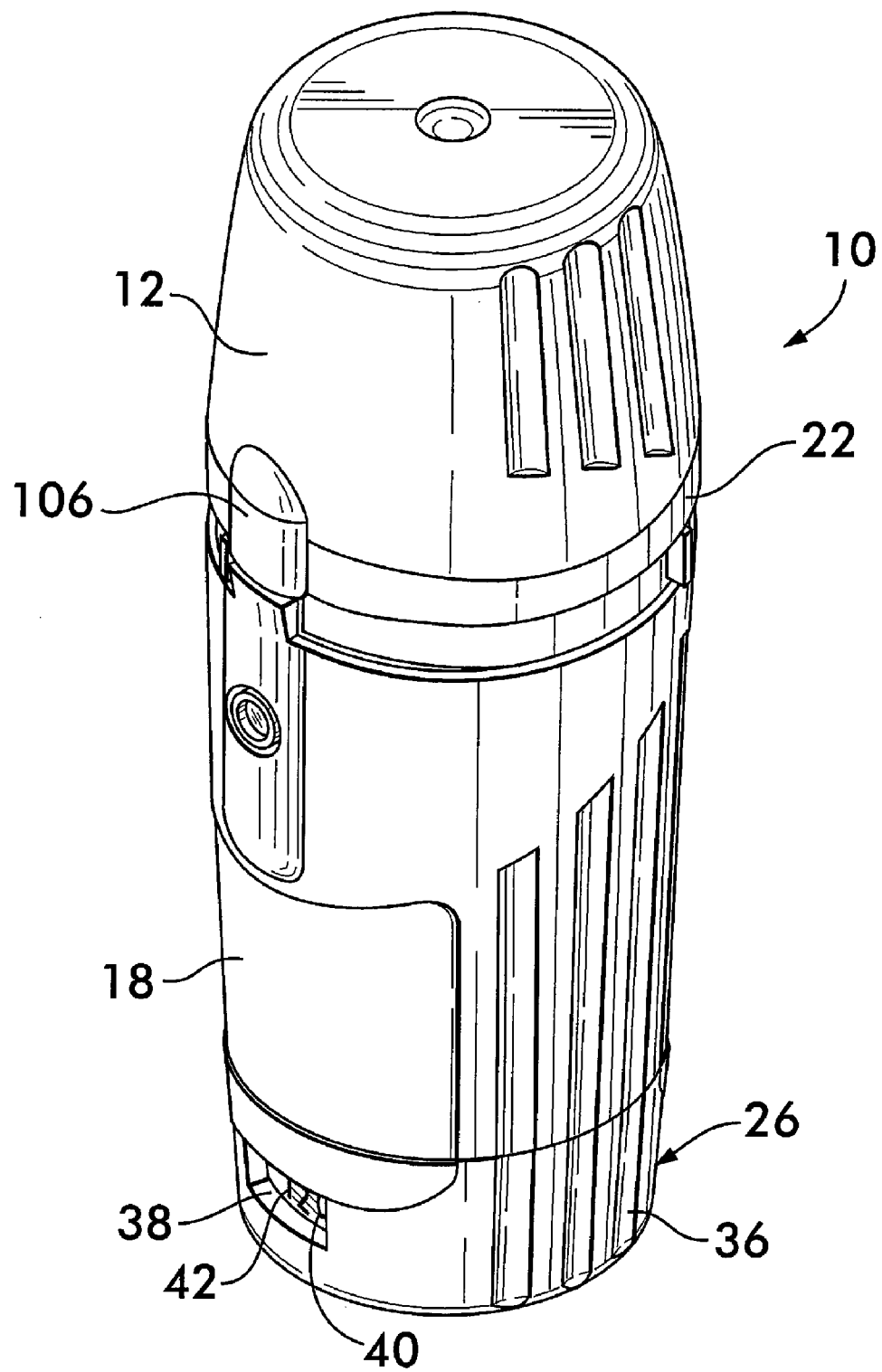
FIG. 1 is a perspective view of the inhaler according to the invention.
Figure 2:
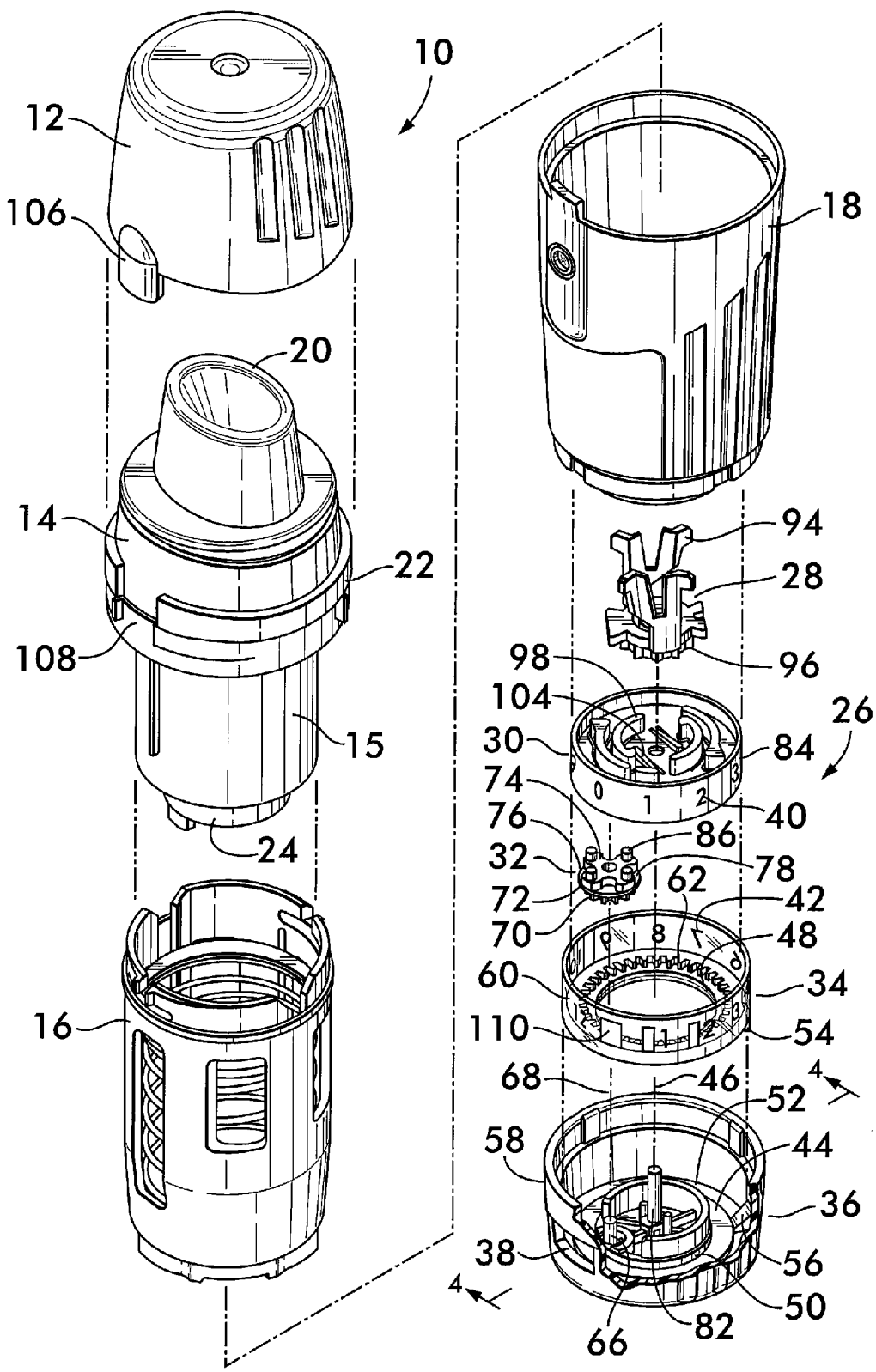
FIG. 2 is an exploded perspective view of the inhaler shown in FIG. 1.

FIG. 1 is a perspective view of a preferred embodiment of an inhaler 10 according to the invention. FIG. 2 is an exploded view of the inhaler 10 shown in FIG. 1. Moving downwardly and from left to right in FIG. 2, the inhaler comprises a dust cap 12, a device core 14 that includes a medicament reservoir 15, a drive sub-assembly 16 and a barrel 18. The device core 14 comprises a mouthpiece 20, a collar 22 and a mandrel 24. Drive sub-assembly 16 fits coaxially within barrel 18, and the mandrel 24 of device core 14 fits coaxially within the drive sub-assembly 16. Collar 22 and mouthpiece 20 on the end of the device core 14 extend outwardly from the drive sub-assembly 16 and barrel 18 to engage the lips of a user as described below.

A counter 26 is mounted onto the inhaler 10 on the end of barrel 18 opposite the dust cap 12. Counter 26 comprises a coupling 28, a unit wheel 30, a slave wheel 32, a tens wheel 34 and a cover 36 in which the unit wheel 30, slave wheel 32 and tens wheel 34 are rotatably mounted. Cover 36 has a window 38 therein through which indicia 40 and 42, printed on the unit and tens wheels respectively, may be viewed, indicating the number of doses remaining in the medicament reservoir 15 or the number of doses dispensed therefrom.

As shown in detail in FIG. 2, cover 36 of counter 26 has a bottom 44 which supports the tens wheel 34 for rotational motion about a central axis 46. Tens wheel 34 has an inwardly extending flange 48 which is sized to surround and engage a raised boss 50 positioned on the bottom 44 concentric with the central axis 46 (see also FIGS. 4 and 4A). Cooperation between the flange 48 and the boss 50 keeps the tens wheel 34 concentric within the cover 36 and allows guided rotation of the tens wheel about the central axis 46. Bottom 44 also has a circular groove 52 positioned concentric with the central axis 46. The groove 52 is sized to accept a tab 54, best shown in FIG. 3. The tab 54 extends downwardly from the tens wheel 34 and tracks within the groove 52 as the tens wheel rotates about central axis 46. As shown in FIG. 2, a stop block 56 is positioned within the groove 52. The stop block 56 engages the tab 54 upon a full rotation of the tens wheel 34 to halt its rotation and thereby prevent the counter from resetting itself after it has counted down to zero and thus give a false reading of the number of doses remaining in the inhaler.

As shown in FIGS. 2 through 4A, an outwardly facing sidewall 58 extends circumferentially around the bottom 44 and is attached to the end of barrel 18 to enclose the counter 26 and mount it onto the inhaler 10. Window 38 is positioned in sidewall 58, allowing viewing of indicia 40 and 42. Indicia 42 are positioned on a radially outwardly facing side surface 60 extending circumferentially around the tens wheel 34. Side surface 60 is positioned concentric with central axis 46 and is adjacent to sidewall 58. Indicia 42 thereon are positioned so as to align with and be visible through the window 38 as the tens wheel rotates within the cover 36. The tens wheel 34 is a decimal wheel showing tens of doses remaining, and thus, the indicia 42 thereon are positioned and spaced apart on the side surface 60 to align to the left side of the window 38, leaving room in the window for indicia 40 on the unit wheel 30 to be displayed through window 38 to the right of the indicia 42 on the tens wheel 34 to properly indicate the unit number of doses remaining.

Figure 3:
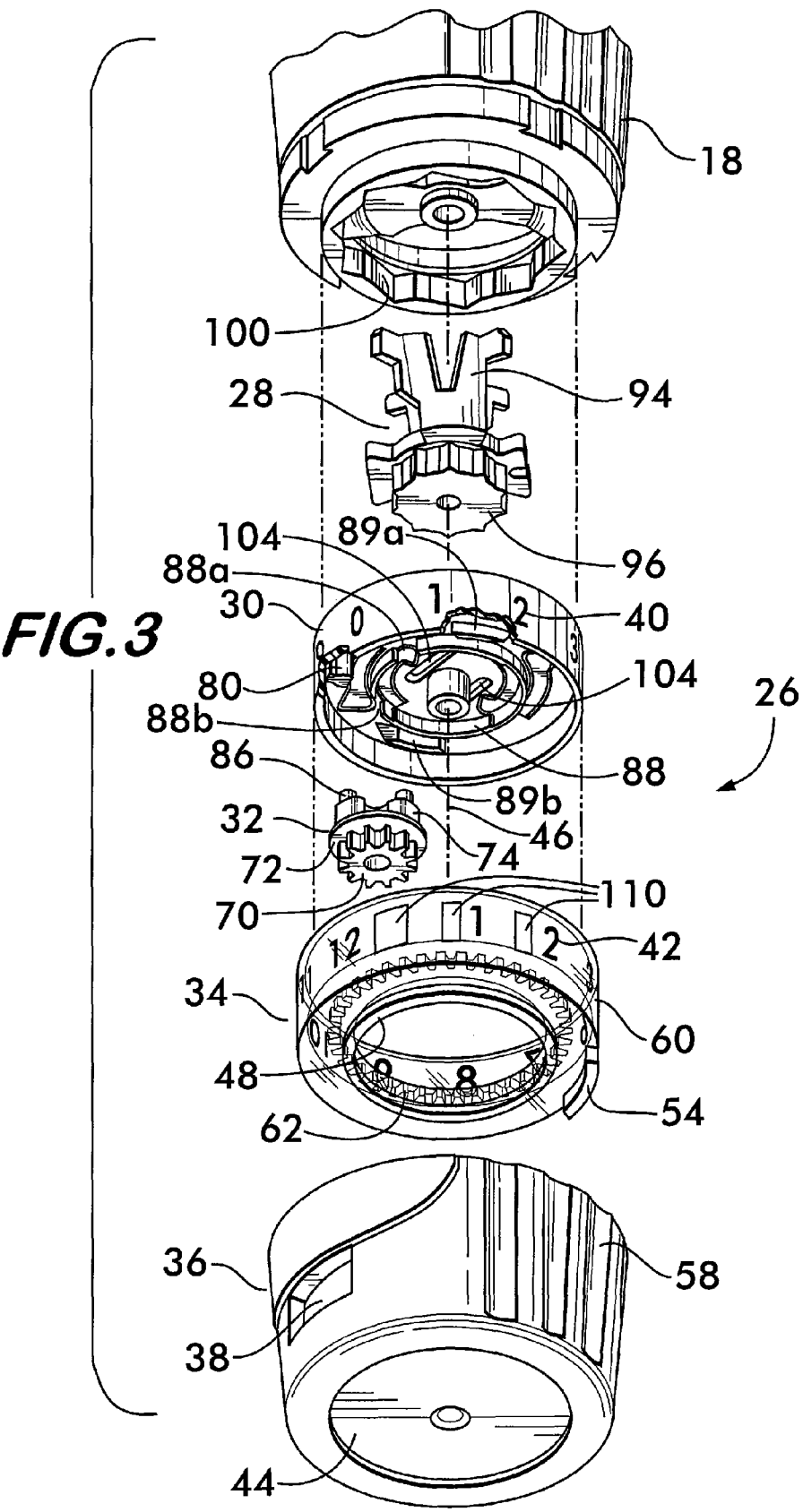
FIG. 3 is a partial exploded perspective view showing the counter for the inhaler.
Figure 6:
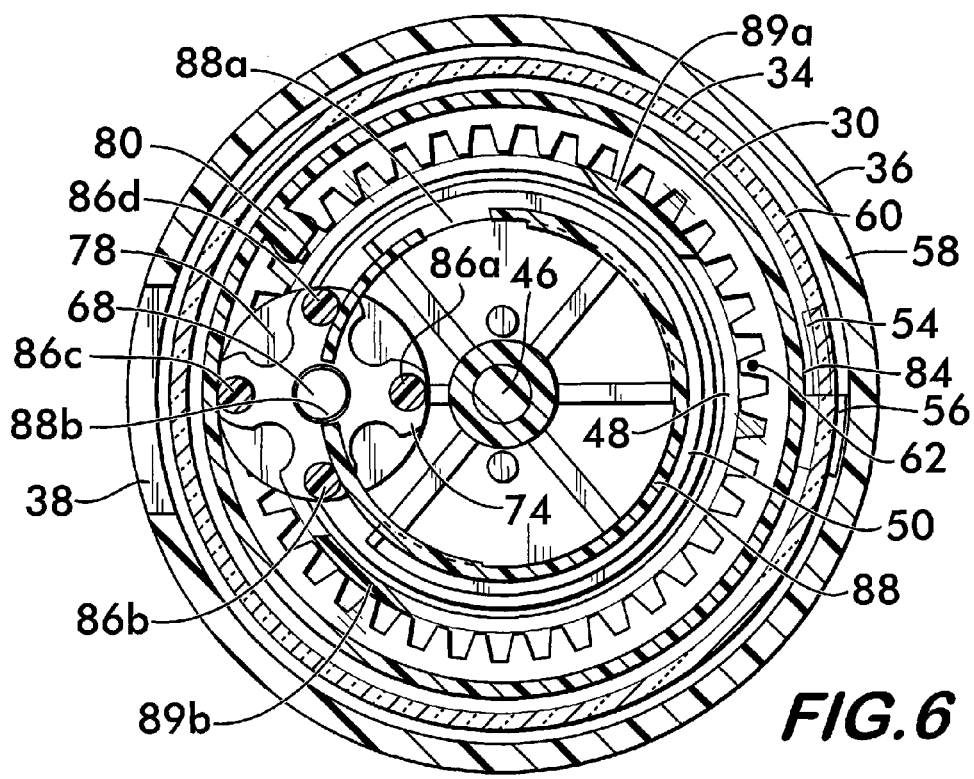

A set of inwardly facing gear teeth 62 are positioned circumferentially around the tens wheel 34 above the flange 48. Gear teeth 62 allow the tens wheel 34 to be driven by the slave wheel 32 positioned between the tens and unit wheels 34 and 30 respectively. As best shown in FIG. 2, slave wheel 32 is mounted on an offset axle 66 extending upwardly from the bottom 44 of the cover 36. Axle 66 is offset from the central axis 46 and thereby provides an offset axis of rotation 68 about which the slave wheel 32 rotates. As shown in FIG. 3, a gear 70 is positioned on one face 72 of the slave wheel 32, the gear 70 meshing with the gear teeth 62 on the tens wheel 34 such that rotation of the slave wheel 32 about the offset axis 68 drives the tens wheel 34 in rotation about the central axis 46 (see also FIG. 11). As shown in FIG. 2, a Geneva mechanism 74 is positioned on the opposite face 76 of the slave wheel 32. As shown in FIG. 6, the Geneva mechanism 74 has a plurality of receptacles 78, four being shown by way of example. The receptacles 78 are positioned in spaced relation circumferentially around the Geneva mechanism. Each receptacle is sized and positioned to receive a foot 80 extending downwardly from the unit wheel (see also FIG. 3). The foot 80 engages one of the receptacles 78 once on each complete revolution of the unit wheel 30, and rotates the slave wheel 32 about the offset axis 68. When the Geneva mechanism 74 has four receptacles 78, it rotates through a 90° rotation about the offset axis 68. Rotation of the slave wheel 32 causes a corresponding rotation of the gear 70 (since both the Geneva mechanism and the gear are on opposite faces of the slave wheel 32) which drives the tens wheel 34 in rotation about central axis 46. The geometry and positioning of the Geneva mechanism 74, gear 70 and the indicia 42 on the tens wheel 34 are such that a 90° rotation of the slave wheel 32 rotates the tens wheel 34 incrementally so that the next indicia 42 is visible within the window 38.

Figure 4:
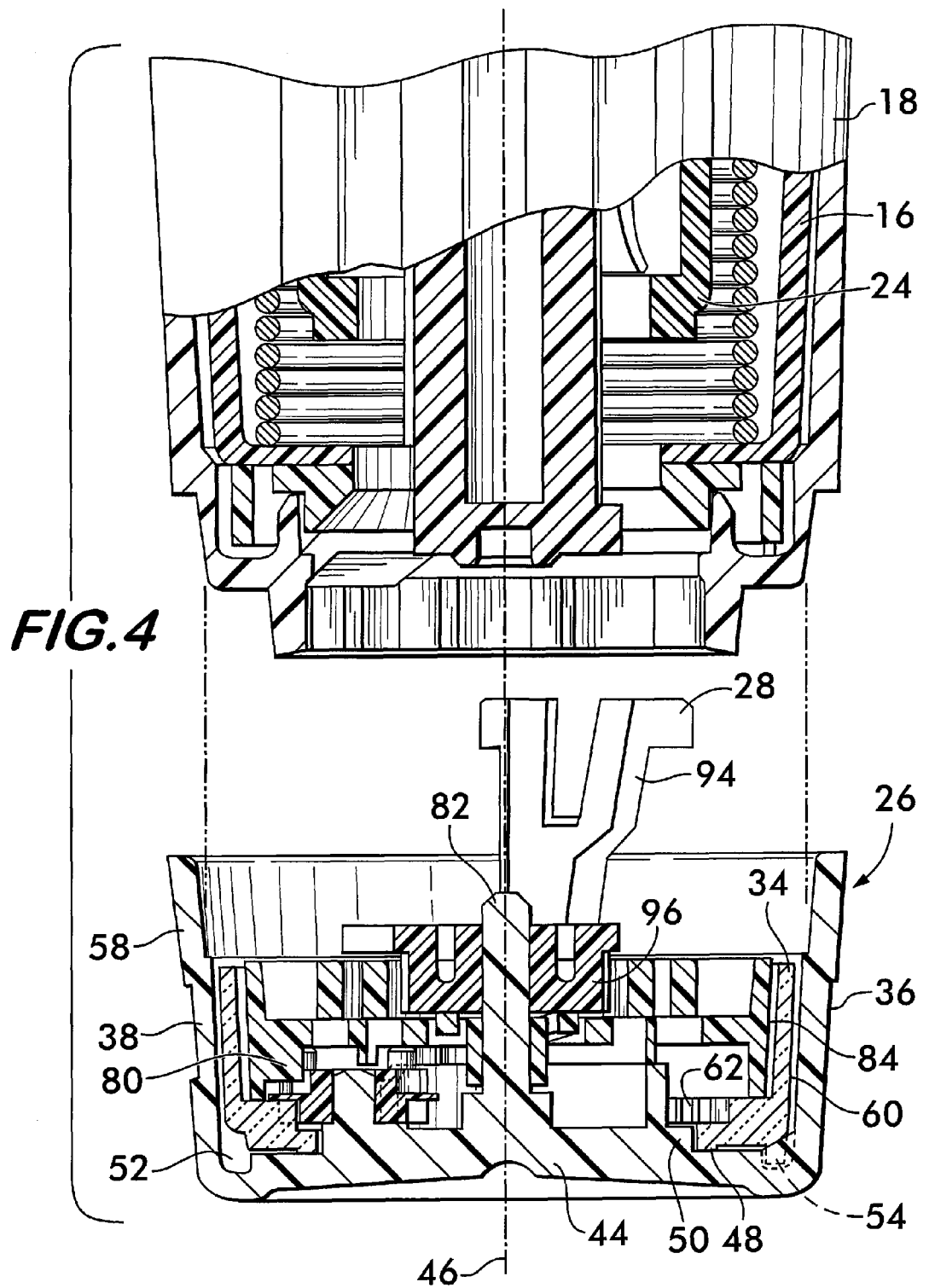
FIG. 4 is an exploded partial sectional view taken at line 4-4 in FIG. 2.
Figure 4A:
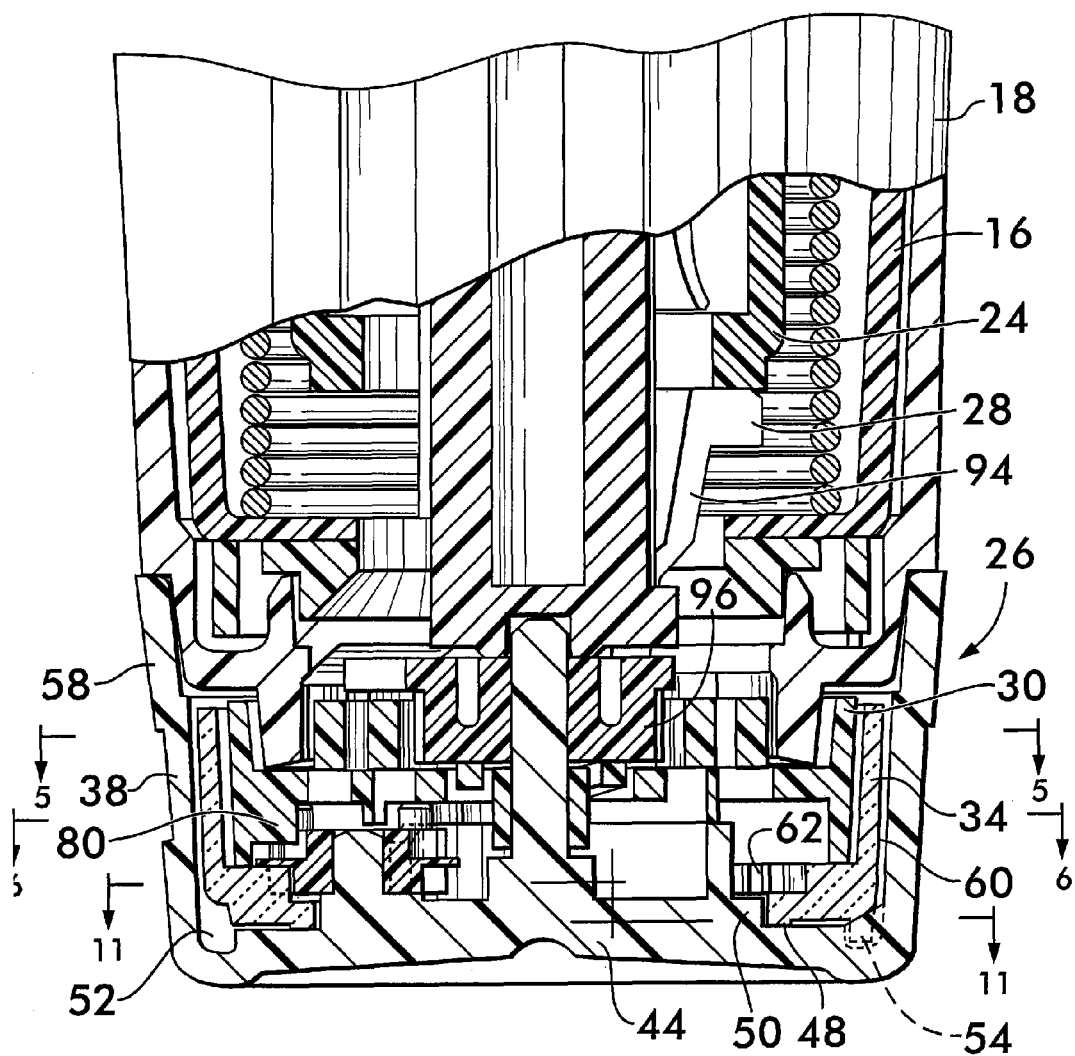
FIG. 4A is a partial sectional view taken at line 4-4 in FIG. 2 with the counter assembled and mounted on the inhaler.

As shown in FIG. 2, unit wheel 30 is rotatably mounted on a central axle 82 substantially aligned with the central axis 46 and extending from the bottom 44 of the cover 36. Unit wheel 30 comprises a radially outwardly facing side surface 84 extending circumferentially around it and upon which the unit indicia 40 are positioned. As shown in FIGS. 4 and 4A, the unit wheel 30 is nested within the tens wheel 34 such that the outwardly facing side surfaces 60 and 84 are coaxial with and adjacent to one another. The side surface 60 on the tens wheel 34 is transparent, thus, allowing the indicia 40 on the unit wheel behind it to be visible. The unit indicia 40 are positioned and spaced around side surface 84 so as to align to the right side of the window 38. Thus, the tens indicia 42 on the tens wheel 34 and the unit indicia 40 on the unit wheel 30 are visible together in the window 38 to show the number of doses remaining or doses already dispensed from the medicament reservoir 15. Positioning the foot 80 on the unit wheel 30 and the gear teeth 62 on the tens wheel 34 is the preferred configuration.

Figure 10:
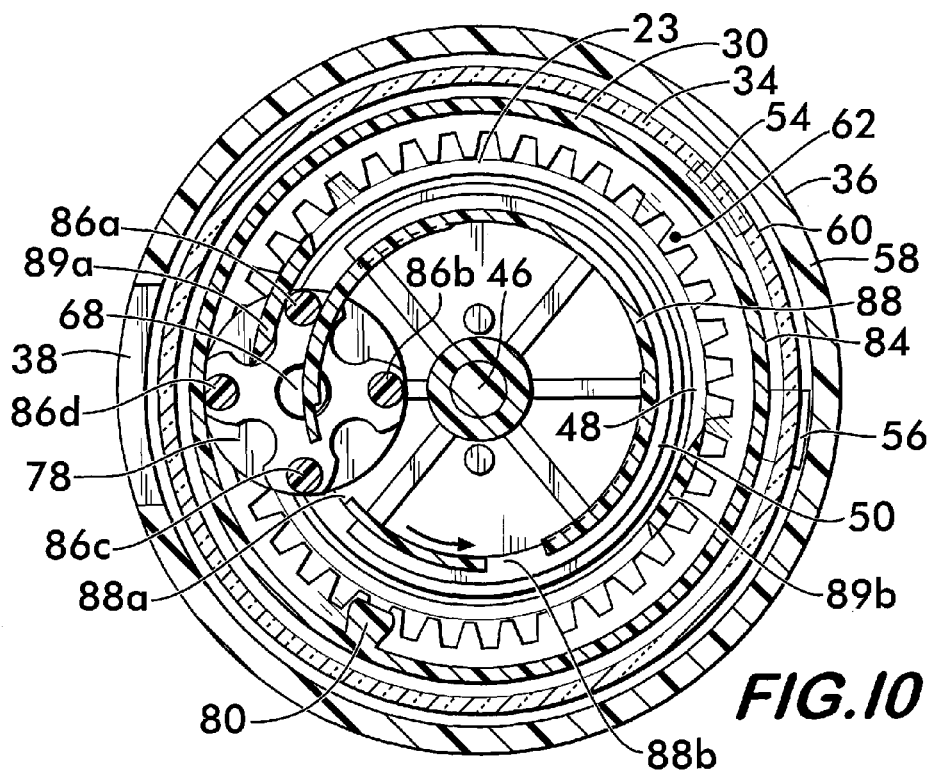

As shown in FIG. 2, slave wheel 32 has a plurality of pins 86 that extend from the Geneva mechanism 74 substantially parallel to the rotation axis 68. Each pin is positioned between two receptacles 78 of the Geneva mechanism. In the example shown, there are four pins 86 and four receptacles 78. As best shown in FIG. 3, an annular wall 88 is positioned on the surface of the unit wheel 30 that faces the slave wheel 32. Wall 88 cooperates with pins 86 to prevent the slave wheel 32 from turning until it is engaged by foot 80 of the unit wheel 30. Wall 88 extends circumferentially around unit wheel 30 and projects from the unit wheel surface substantially parallel to axis 46. The wall is coaxial with axis 46 and has a height allowing it to be engaged by pins 86 to prevent slave wheel rotation as best shown in FIG. 6. There are two openings, 88a and 88b, in wall 88. Each opening is positioned flanking the foot 80 as shown in FIG. 6. The openings permit pins 86 to pass through the wall 88 and thereby allow the slave wheel 32 to rotate when the foot 80 engages one of the receptacles 78. As shown in FIG. 3, two wall segments 89a and 89b also extend from the unit wheel. Wall segments 89a and 89b are positioned in spaced relation radially outwardly from wall 88. The wall segments are preferably curved and have axis 46 as their center of curvature. The wall segments 89a and 89b are angularly displaced from openings 88a and 88b respectively, and also engage pins 86 to prevent rotation of the slave wheel. This is necessary when one of the pins is aligned with either opening 88a or 88b and foot 80 is not engaged with a receptacle 78 as shown in FIG. 10 and described in detail below.

As shown in FIG. 2, the unit wheel 30 is driven by coupling 28 which couples the motion of the mandrel 24 of the device core 14 to the counter 26. Coupling 28 has a plurality of legs 94 which extend from the counter 26 into the barrel 18 and engage tabs on the mandrel 24 of the device core 14. Legs 94 are arranged in spaced relation to one another so as to provide for lost motion between the mandrel 24 and the coupling 28. The lost motion allows for the large rotational motion of the device core 14 relative to the drive sub-assembly 16 needed to actuate the inhaler, yet also provides a reduced rotational motion of the device core 14 relative to the counter 26 needed to actuate the counter. Legs 94 are flexible and, thus, may be resiliently bent to facilitate assembly of the counter onto the inhaler by allowing the legs to flex and be inserted into barrel 18.

Figure 5:
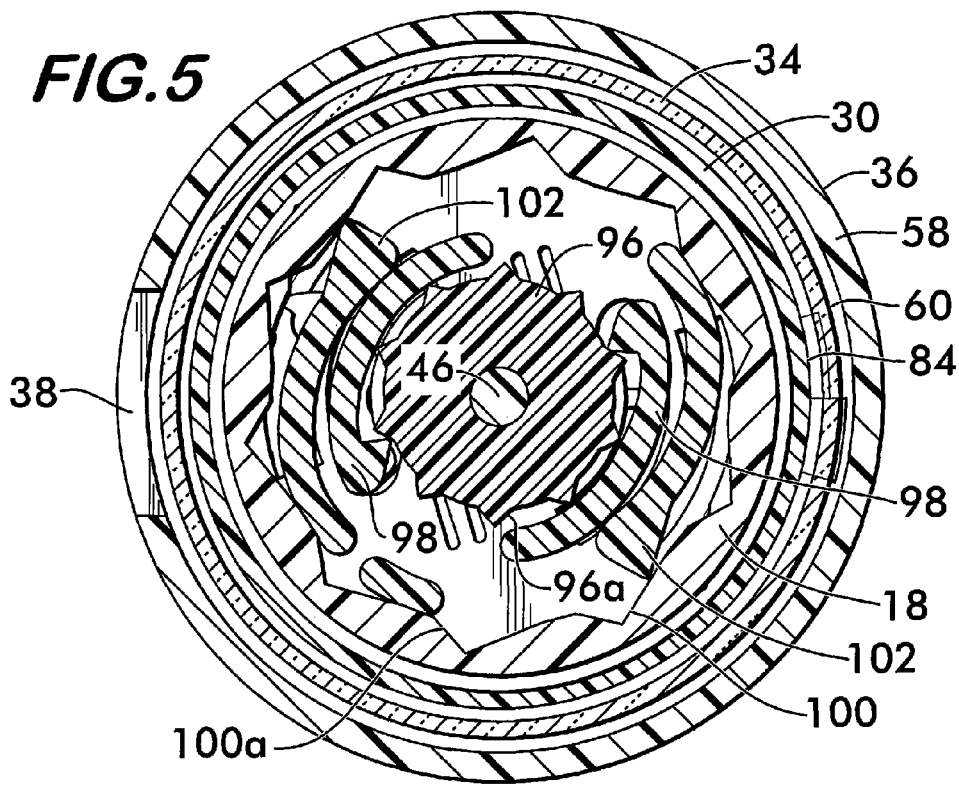
FIG. 5 is a cross-sectional view taken at line 5-5 in FIG. 4A.

Mounted on the coupling 28 opposite to the legs 94 is a ratchet 96 which engages pawls 98 on the unit wheel 30 (see also FIG. 5). Thus, motion of the device core 14 relative to the barrel 18 as the inhaler is actuated is transmitted from the mandrel 24 to the unit wheel 30 by means of the legs 94, the ratchet 96 and the pawls 98 on the unit wheel 30. The ratchet and pawl are used to move the unit wheel only in one direction to decrement (or increment) the counter for each actuation. As described in detail below, actuation of the inhaler 10 requires a reciprocal motion of the device core 14 relative to the barrel 18, and the reciprocal motion must be converted to unidirectional motion of the counter 26, and this is effected by means of the ratchet 96 and pawls 98. The position of the ratchet 96 on the coupling 28 and pawls 98 on the unit wheel 30 are preferred for ease of manufacture but could easily be reversed and achieve the same desired effect.

As shown in FIG. 3, a second ratchet 100 is positioned on the end of barrel 18. As shown in FIG. 5, the ratchet 100 faces radially inwardly to engage pawls 102 which are mounted on the unit wheel 30 and face outwardly to engage the ratchet 100. Ratchet 100 and pawls 102 work in cooperation with ratchet 96 and pawls 98 to prevent retrograde motion of the unit wheel when it is actuated by the reciprocal motion of the device core 14 relative to the barrel 18. The cooperation of the ratchets and pawls is described in detail below in the description of counter operation. Uni-directional motion of the unit wheel is ensured by proper design of the ratchet angles and relative panel lengths of the ratchets 96 and 100 and pawls 98 and 102.

As illustrated in FIG. 3, unit wheel 30 also has a plurality of cantilevered fingers 104 which extend upwardly from the unit wheel and engage the coupling 28. The fingers 104 act as springs to bias the components of the counter 26 against the bottom 44 of cover 36. When compressed against the coupling 28, the unit wheel 30 is biased against the tens wheel 34, keeping the slave wheel 32 properly positioned and engaged with the unit and tens wheels. The biasing action of the fingers 104 also keeps the tens wheel 34 properly seated on the bottom 44 concentric with boss 50 and generally ensures smooth operation of the counter and also helps prevent powdered medicament from contaminating the counter mechanism.

It is preferred to make the inhaler and counter from plastic materials for cost effective manufacture by injection molding. For example, the barrel 18, cover 26 and cap 12 may be polypropylene, while the unit wheel and tens wheel are preferably polycarbonate. The coupling and slave wheel may be polybutylene terephthalate, and the device core is predominantly made of an acetal homopolymer such as Delrin®.

Inhaler and Counter Operation

Operation of the inhaler 10 is described in detail in U.S. Pat. No. 5,678,538 to Drought, which is hereby incorporated by reference. Provided below is a simplified explanation of inhaler operation as it relates to the counter 26.

With reference to FIG. 2, to administer a metered dose of powdered medicament, a user grasps the barrel 18 in one hand and the dust cap 12 in the other. The cap 12 and barrel 18 are rotated relatively to one another through an angle of about 105° about the central axis 46 with the cap 12 rotating clockwise and the barrel counterclockwise when viewed from the cap end of the inhaler. Cap 12 has a tab 106 which engages a notch 108 in collar 22, causing the entire device core 14 to rotate clockwise along with the cap 12. The cap 12 and barrel 18 are then relatively rotated in the reverse direction through the same angle. The reciprocal rotation of the cap 12 and device core 14 causes a metered dose of powdered medicament to be scraped from the reservoir and deposited in the device core 14. The user removes the cap 12, places his or her lips to the mouthpiece 20 and inhales. The medicament becomes entrained in an air stream drawn through the mouthpiece 20 and is drawn into the mouth, trachea and lungs of the user where it is absorbed.

The relative rotation between the barrel 18 and the device core 14 is used to actuate the counter 26. By way of example only, a decrementing counter, which counts down and indicates the number of doses remaining within the reservoir, is described below, it being understood that an incrementing counter, which counts upward and indicates the number of doses administered, functions in essentially the same way as the decrementing counter. References to clockwise and counterclockwise rotations which follow are defined as if viewed from the dust cap 12 of the inhaler along central axis 46.

The initial clockwise rotation of the device core 14 cuts a dose of medicament from the reservoir 15 and loads it into the device core. This clockwise rotation extends through about 105° and is transmitted to the unit wheel 30 by the coupling 28. Legs 94 engage the mandrel 24 on the device core to transmit the motion. There is lost motion between the legs 94 and the mandrel 24 over an angle of about 56.5°. After this point in the rotation, the mandrel contacts the legs and rotates the coupling 28 through an angle of about 48.5° clockwise. As shown in FIG. 5, ratchet 96 on the coupling is rotated clockwise relatively to pawls 98 on the unit wheel, the pawls 98 slipping over the ratchet teeth 96a and clicking into place on the other side of the teeth, ready to move the unit wheel 30 upon the reverse rotation of the air channel assembly 14. The unit wheel 30 is prevented from rotating clockwise as the pawls 98 engage and slip over the teeth 96a by the second ratchet 100 located in barrel 18, engaged by outer pawls 102 on the unit wheel 30. Note that the pawls 98 are stressed in bending only during motion of the coupling 28 relative to the unit wheel. At all other times, the pawls remain unstressed and, thus, will not take on a permanent set which could adversely affect the ratcheting action of the mechanism.

The user then turns the cap 12 relative to the barrel 18 through a counterclockwise rotation of about 105°, isolating the dose of medicament from the reservoir and also causing the counter to decrement one unit. Again, there is lost motion between the mandrel 24 and the coupling 28 over about 56.5° of the rotation. After this point, the mandrel 24 causes the coupling 28 to rotate counterclockwise through an angle of about 48.5°. During this rotation, ratchet 96 (see FIG. 5), rotating counterclockwise, engages pawls 98 on the unit wheel 30 and rotates the unit wheel counterclockwise about the central axis 46 so that the next lower value of the indicia 40 is displayed in the window 38. There is lost motion between the ratchet 96 and pawls 98 such that the unit wheel 30 is rotated though an angle of 36°, thus, providing ten decrements of the unit wheel over a complete revolution through 360°. The lost motion is obtained by appropriate spacing of the ratchet teeth 96a. Upon counterclockwise rotation of the unit wheel 30, the pawls 102 slip over the ratchet teeth 100a to engage the next teeth and lock the unit wheel in place until the next dose is loaded by the clockwise rotation of the device core 14 relative to the barrel 18.

As may be deduced from FIG. 6, for most of a rotation of the unit wheel 30, two pins, in this instance, 86b and 86d of the slave wheel engage wall 88, and this prevents the slave wheel from inadvertently turning and rotating the tens wheel in error. FIG. 6 shows the unit wheel 30 in an orientation where foot 80 is approaching a receptacle 78 of the Geneva mechanism 74. Engagement of the foot with the receptacle occurs once per revolution of the unit wheel and rotates the tens wheel 34 by one increment as described below.

As shown in FIG. 7, unit wheel 30 has advanced further, causing foot 80 to engage a receptacle 78 on Geneva mechanism 74, rotating the slave wheel counterclockwise. This occurs on each tenth incremental rotation of unit wheel 30 in this example. Rotation of the slave wheel is permitted in this instance because opening 88b rotates with the unit wheel and aligns with pin 86b and allows the pin to pass through wall 88.

As shown in FIG. 8, further rotation of the unit wheel 30 continues to rotate the slave wheel, and is permitted because pin 86a aligns with opening 88a and the pin passes through this opening in the wall 88. Counterclockwise motion of the unit wheel 30 causes counterclockwise rotation of the slave wheel 32 about the offset axis 68, and this in turn effects an incremental rotation of the tens wheel 34 through the gear 70 on the slave wheel 32 (see FIG. 3) engaging the gear teeth 62 on the tens wheel.

Figure 9:
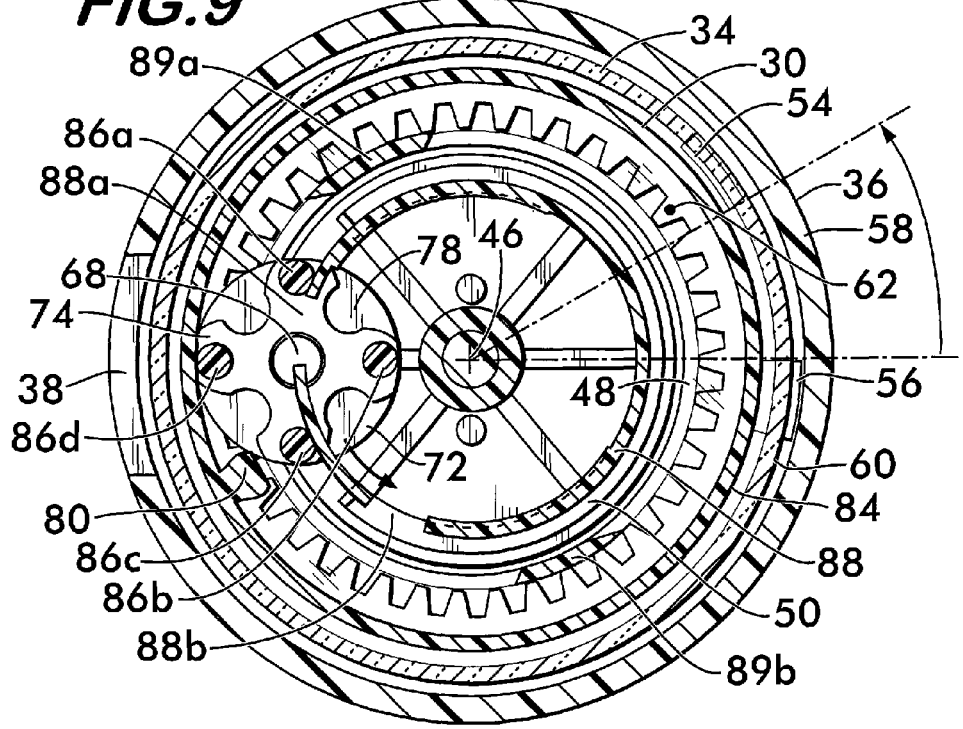

With continued rotation of the unit wheel 30, as shown in FIG. 9, the foot 80 disengages from the receptacle 78 and pins 86a and 86c now engage wall 88 for the next revolution of the unit wheel, again preventing rotation of the slave wheel 32.

In the course of the rotation of the unit wheel 30, a configuration, shown in FIG. 10, is periodically reached where one of the pins (86c in this instance) is positioned adjacent to an opening (88a) in the wall 88, the other pin (86a) remaining engaged with the wall. In this configuration, it would be possible for the slave wheel to rotate counterclockwise, because only one pin engages wall 88, the other pin (86c) being able to pass through the opening 88a and thus being ineffective against blocking rotation of the slave wheel. However, with the foot 80 disengaged from a receptacle of the Geneva mechanism, it is still desired to prevent rotation of the slave wheel 32 to prevent inadvertent rotation of tens wheel 34. To ensure that the slave wheel does not rotate when only one pin 86 is engaged with wall 88, the wall segments 89a and 89b are provided. Wall segment 89a is positioned so that pin 86a is constrained between it and wall 88 when another pin (86c) is adjacent to an opening (88a) in the wall and the foot 80 is not yet engaged with the receptacle 78 of the Geneva mechanism 74. Wall segment 89b performs the same function when a pin aligns with opening 88b.

Figure 11:
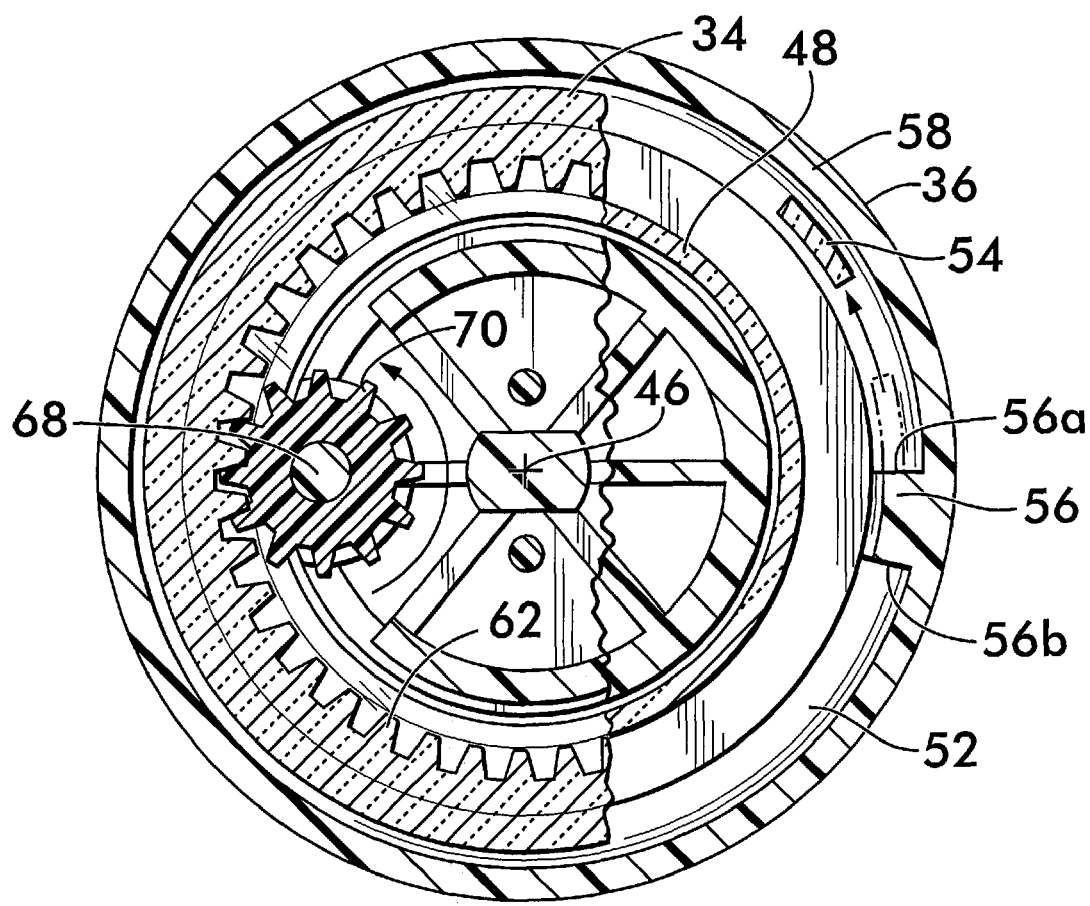
FIG. 11 is a cross-sectional view taken at line 11-11 in FIG. 4A.

Over the 36° of rotation of the unit wheel 30, the first and last 3° are lost motion relative to the slave wheel 32, and the middle 30° rotates the slave wheel through 90°. As shown in FIG. 11, gear 70 on the slave wheel 32 also rotates counterclockwise through 90°, its teeth engaging the gear teeth 62 on the tens wheel 34, and causing a counterclockwise rotation of the tens wheel 34 about the central axis 46 to bring the next lower indicia 42, indicating tens of doses, into view within the window 38. Indicia 40 on the unit wheel 30 are visible through the transparent tens wheel 34 and align with the indicia 42 on the tens wheel and together indicate the number of doses remaining. The gear ratio between gear 70 and the tens wheel 34 is designed to move the tens wheel in proportion to the number of divisions, indicated by the indicia 42, on the tens wheel 34. For example, a dose counter having 120 doses will require 13 divisions, corresponding to indicia from 1-12 and a blank space indicating zero, positioned on the tens wheel 34. Thus, with each complete revolution of the unit wheel (with ten divisions numbered 0-9), the tens wheel 34 should move through an incremental angle of about 27.7° ($\frac{1}{13}$ of a complete revolution). Note that this rotation must be achieved by a 90° rotation of the gear 70. A ratio of about 3.25 to 1 between the tens wheel 34 and the gear 70 will cause the desired rotation of the tens wheel 34. As best shown in FIG. 3, it is advantageous to provide colored indicators 110 on the tens wheel 34 positioned near the low numbered indicia 42 to provide a readily visible warning that few doses remain in the inhaler.

A complete repeat revolution of the tens wheel 34 is prevented by the engagement of tab 54 with the stop block 56 positioned within the circular groove 52 in the bottom 44 of cover 36 (see FIGS. 2 and 11). As shown in FIG. 11, tab 54 is initially positioned adjacent to one side 56a of the stop block 56 (the position corresponding to the maximum indicia 42 being aligned within window 38) and initially moves counterclockwise away from the stop block as the tens wheel 34 rotates. When fewer than ten doses remain within the inhaler, the space on the tens wheel 34 aligned within window 38 is blank, displaying one of the colored indicators 110, and the tab 54 is engaged with the opposite side 56b of the stop block 56. This prevents any additional rotation of the tens wheel 34 after the final ten decrements of the unit wheel, thus, preventing the counter 26 from resetting itself by aligning the maximum tens indicia 42 within the window, which would occur if the tens wheel 34 were permitted to revolve beyond the complete revolution. However, even though the counter indicates no doses remaining, there may still be sufficient medicament in the reservoir to provide additional therapeutic doses to the user. The inhaler is designed so that the counter 26 may be overridden to administer any additional doses remaining after zero doses are indicated. Override of the counter is possible due to the design of ratchet 96 and pawls 98 (FIG. 5). When the tens wheel 34 is prevented from turning, and upon application of sufficient torque by the user turning the cap 12, the pawls 98 will slip over the ratchet teeth 96a as the coupling 28 moves in the counterclockwise direction, thereby allowing a medicament dose to be loaded into the air channel assembly without actuating the counter 26. Normally, the pawls 98 engage the teeth 96a of ratchet 96 when the ratchet turns in the counterclockwise direction to actuate the counter 26. However, the pawls 98 are sufficiently flexible such that they will disengage from the ratchet rather than jam the entire inhaler mechanism when sufficient torque is applied and the tens wheel 34 is blocked by the stop block 56.

The inhaler and counter according to the invention provides a compact, inexpensive and reliable means for administering measured doses of a powdered medicament, while knowing with a significant degree of precision how many doses are remaining in the inhaler at any given time and when an inhaler should be replaced with a new one.

What is claimed is:

1. A rotatably actuated counter mechanism, comprising:
   a first wheel rotatable about a first axis of rotation, said first wheel having a first display surface extending circumferentially there around for displaying counting indicia thereon, said first wheel also having a plurality of gear teeth extending circumferentially there around;
   a second wheel also rotatable about said first axis, said second wheel having a second surface extending circumferentially there around for displaying counting indicia thereon, said second wheel having a wall projecting in a direction substantially parallel to and substantially surrounding said first axis, said wall having a plurality of openings therethrough, said second wheel also having a foot projecting therefrom in a direction substantially parallel to said first axis;
   a slave wheel positioned between said first and second wheels, said slave wheel being rotatable about a second axis of rotation offset laterally from said first axis, a gear being positioned on one face of said slave wheel, said gear being engaged with said gear teeth of said first wheel, said first wheel being rotated about said first axis upon rotation of said slave wheel about said second axis, a Geneva mechanism being positioned on an opposite face of said slave wheel, said Geneva mechanism having a plurality of receptacles adapted to receive said foot projecting from said second wheel, engagement of said foot with one of said receptacles incrementally rotating said slave wheel in response to rotation of said second wheel and thereby incrementally rotating said first wheel, a plurality of pins being mounted in spaced relation around said Geneva mechanism, said pins projecting in a direction parallel to said second axis and being engageable with said wall, said pins aligning with and passing through said openings in said wall when said foot engages one of said receptacles, said pins otherwise engaging said wall, engagement of said pins and said wall preventing rotation of said slave wheel and thereby said first wheel.

2. A counter mechanism according to claim 1, further comprising:
   a plurality of wall segments positioned on said second wheel in spaced apart relation to said wall and projecting in a direction substantially parallel to said first axis, said wall segments being positioned relatively to said openings in said wall such that one of said pins projecting from said Geneva mechanism is positioned between said wall and said wall segment when another of said pins is positioned adjacent to an opening of said wall.

3. A counter mechanism according to claim 1, wherein said first and second display surfaces face radially outwardly from said first axis.

4. A counter mechanism according to claim 3, wherein said first wheel is positioned in overlying relation with said second wheel, said first display surface being transparent and surrounding said second display surface, each of said indicia on said first display surface representing ten units, each of said indicia on said second surface representing one unit, said indicia on said surfaces cooperating to indicate a total number of units counted by said counter.

5. A counter mechanism according to claim 4, further comprising:
   a housing having a bottom, said first wheel being rotationally supported thereon;
   an axle extending from said bottom and oriented coaxially with said first axis of rotation, said second wheel being rotatably mounted on said axle;
   an offset axle extending from said bottom and oriented coaxially with said second axis of rotation, said slave wheel being rotatably mounted on said offset axle;
   a sidewall attached to said bottom and surrounding said first and second wheels, a window being positioned within said sidewall, indicia on said first and second wheels being visible through said window, said visible indicia being indicative of a count registered by said counter.

6. A counter mechanism according to claim 1, wherein said second wheel rotates through ten increments for every one incremental rotation of said first wheel.

7. A counter mechanism according to claim 1, wherein said Geneva mechanism has four receptacles spaced at substantially equal angular intervals around said Geneva mechanism and four pins, each pin being positioned between two of said receptacles.

8. A counter mechanism according to claim 1, wherein said gear teeth on said first wheel face inwardly toward said first axis and said gear on said slave wheel has teeth facing outwardly from said second axis.

9. A mechanism, comprising:
   a slave wheel rotatable about an axis of rotation, said slave wheel having first and second faces oppositely disposed, said axis being oriented substantially perpendicular to said faces;
   a toothed gear mounted on said first face, said teeth projecting substantially radially outwardly from said axis;
   a Geneva mechanism mounted on said second face, said Geneva mechanism having a plurality of receptacles extending in spaced relation circumferentially therearound, each receptacle having an opening facing substantially radially outwardly from said axis;
   a plurality of pins positioned on said Geneva mechanism between said receptacles, said pins projecting in a direction substantially parallel to said axis.

10. A mechanism according to claim 9, wherein said Geneva mechanism comprises four of said receptacles spaced at substantially equal angular intervals around said slave wheel.

11. A mechanism according to claim 10, wherein said Geneva mechanism comprises four of said pins.

12. A mechanism according to claim 9, wherein said slave wheel has a centrally located aperture for rotatably mounting said slave wheel on an axle parallel to said axis of rotation.

13. A dry powder inhaler for administering a dose of a medicament, said inhaler comprising:
   a reservoir holding said medicament;
   a device core engaged with and rotatably movable relatively to said reservoir for receiving said dose of medicament upon said relative motion;
   a rotatably actuated counter mechanism for counting a number of doses dispensed or remaining in said reservoir, said counter mechanism comprising:

a first wheel rotatable about a first axis of rotation, said first wheel having a first display surface extending circumferentially there around for displaying counting indicia thereon, said first wheel having a plurality of gear teeth extending circumferentially there around;

a second wheel also rotatable about said first axis, said second wheel having a second surface extending circumferentially there around for displaying counting indicia thereon, said second wheel having a wall projecting in a direction substantially parallel to and substantially surrounding said first axis, said wall having a plurality of openings therethrough, said second wheel also having a foot projecting therefrom in a direction substantially parallel to said first axis;

a coupling extending between said device core and said second wheel for transmitting rotational motion of said device core to said second wheel, said rotational motion being indicative of a dose of said medicament delivered from said reservoir;

a slave wheel positioned between said first and second wheels, said slave wheel being rotatable about a second axis of rotation offset laterally from said first axis, a gear being positioned on one face of said slave wheel, said gear being engaged with said gear teeth of said first wheel, said first wheel being rotated about said first axis upon rotation of said slave wheel about said second axis, a Geneva mechanism being positioned on an opposite face of said slave wheel, said Geneva mechanism having a plurality of receptacles adapted to receive said foot projecting from said second wheel, engagement of said foot with one of said receptacles incrementally rotating said slave wheel in response to rotation of said second wheel and thereby incrementally rotating said first wheel, a plurality of pins being mounted in spaced relation around said Geneva mechanism, said pins projecting in a direction along said second axis and being engageable with said wall, said pins aligning with and passing through said openings in said wall when said foot engages one of said receptacles, said pins otherwise engaging said sidewall, engagement of said pins and said sidewall preventing rotation of said slave wheel and said first wheel.

14. An inhaler according to claim 13, further comprising:

a plurality of wall segments positioned on said second wheel in spaced apart relation to said wall and projecting in a direction substantially parallel to said first axis, said wall segments being positioned relatively to said openings in said wall such that one of said pins projecting from said Geneva mechanism is positioned between said wall and said wall segment when another of said pins is positioned adjacent to an opening of said wall.

15. An inhaler according to claim 13, wherein said first and second display surfaces face radially outwardly from said first axis.

16. An inhaler according to claim 15, wherein said first wheel is positioned in overlying relation with said second wheel, said first display surface being transparent and surrounding said second display surface, each of said indicia on said first display surface representing ten units, each of said indicia on said second surface representing one unit, said indicia on said surfaces cooperating to indicate a total number of units counted by said counter mechanism.

17. An inhaler according to claim 16, further comprising:

a housing mounted on said inhaler, said housing having a bottom, said first wheel being rotationally supported thereon;

an axle extending from said bottom and oriented coaxially with said first axis of rotation, said second wheel being rotatably mounted on said axle;

an offset axle extending from said bottom and oriented coaxially with said second axis of rotation, said slave wheel being rotatably mounted on said offset axle;

a sidewall attached to said bottom and surrounding said first and second wheels, a window being positioned within said sidewall, indicia on said first and second wheels being visible through said window, said visible indicia being indicative of a count registered by said counter mechanism.

18. An inhaler according to claim 13, wherein said second wheel rotates through ten increments for every one incremental rotation of said first wheel.

19. An inhaler according to claim 13, wherein said Geneva mechanism has four receptacles spaced at substantially equal angular intervals around said Geneva mechanism and four pins, each pin being positioned between two of said receptacles.

20. An inhaler according to claim 13, wherein said gear teeth on said first wheel face inwardly toward said first axis and said gear on said slave wheel has teeth facing outwardly from said second axis.

* * * * *